(12) United States Patent
Wang et al.

(10) Patent No.: US 8,273,344 B2
(45) Date of Patent: Sep. 25, 2012

(54) RECOMBINANT ADENO-ASSOCIATED VIRUS EXPRESSING HUMAN ANTISENSE GENE CYP2J2 AND ITS PREPARATION METHODS

(75) Inventors: Daowen Wang, Wuhan (CN); Jiangang Jiang, Wuhan (CN); Xiao Xiao, Wuhan (CN)

(73) Assignees: Tongji Hospital, Wuhan (CN); Tongji Medical College, Wuhan (CN); Huazhong University of Science and Technology, Wuhan (CN)

( * ) Notice: Subject to any disclaimer, the term of this patent is extended or adjusted under 35 U.S.C. 154(b) by 463 days.

(21) Appl. No.: 11/720,035

(22) PCT Filed: Nov. 28, 2005

(86) PCT No.: PCT/CN2005/002040
§ 371 (c)(1),
(2), (4) Date: May 23, 2007

(87) PCT Pub. No.: WO2006/058489
PCT Pub. Date: Jun. 8, 2006

(65) Prior Publication Data
US 2008/0131403 A1    Jun. 5, 2008

(30) Foreign Application Priority Data
Nov. 30, 2004  (CN) .......................... 2004 1 0061237

(51) Int. Cl.
*C12N 15/864* (2006.01)
*C12N 15/113* (2010.01)
*C12N 15/09* (2006.01)
*C12N 15/00* (2006.01)

(52) U.S. Cl. ..................... 424/93.2; 424/93.6; 536/24.5; 435/320.1

(58) Field of Classification Search .................. None
See application file for complete search history.

(56) References Cited

U.S. PATENT DOCUMENTS

| | | | | |
|---|---|---|---|---|
| 2002/0128438 | A1* | 9/2002 | Seol et al. | 530/350 |
| 2003/0092658 | A1* | 5/2003 | Meyers et al. | 514/44 |
| 2004/0110733 | A1* | 6/2004 | Borlak et al. | 514/171 |

OTHER PUBLICATIONS

Bennett and Cowsert, Antisense oligonucleotides as a tool for gene functionalization and target validation, Biochimica et Biophysica Acta 1489 (1999) 19-30.*

* cited by examiner

*Primary Examiner* — Maria Marvich
(74) *Attorney, Agent, or Firm* — Matthias Scholl, P.C.; Matthias Scholl

(57) ABSTRACT

A recombinant adeno-associated virus (rAAV) expressing antisense human CYP2J2 gene produced by a method of co-transfection into 293 cell by calcium phosphate precipitation, the rAAV having the following three plasmids: a) pXX$_2$: a packing plasmid having a nucleotide sequence encoding AAV Rep and Cap protein, wherein the nucleotide sequence is operably linked upstream and downstream to a p5 promoter respectively to increase expression 15-fold; b) pXXUF$_1$-anti2J2: an eukaryotic expression vector having a CMV promoter, a NotI site for insertion of target genes, the CYP2J2 gene oriented in the 3' to 5' direction, and inverted terminal repeats (ITRs); and c) pXX$_6$: a helper plasmid deleted of the pathogenic gene sequences of adenovirus and having an E1A, an E2A, and a VA1 RNA gene of adenovirus. Also provided is a method of preparing the rAAV.

1 Claim, 18 Drawing Sheets

```
  1 ccacgcgtcc gcgccgcctg cttggaccgc agaagagcag gaggacgtct gagccatgct
 61 cgcggcgatg ggctctctgg cggctgccct ctgggcagtg gtccatcctc ggactctcct
121 actgggcact gtcgcctttc tgctcgctgc tgactttctc aaaagacggc gcccaaagaa
181 ctacccgccg gggccctggc gcctgccctt ccttggcaac ttcttccttg tggacttcga
241 gcagtcgcac ctggaggttc agctgtttgt gaagaaatat gggaaccttt ttagcttgga
301 gcttggtgac atatctgcag ttcttattac tggcttgccc ttaatcaaag aagcccttat
361 ccacatggac caaaactttg ggaaccgccc cgtgacccct atgcgagaac atatctttaa
421 gaaaaatgga ttgattatgt caagtggcca ggcatggaag gagcaaagaa ggttcactct
481 gacagcacta aggaactttg gtttaggaaa gaagagctta gaggaacgca ttcaggagga
541 ggcccaacac ctcactgaag caataaaaga ggagaacgga cagccttttg accctcattt
601 caagatcaac aatgcagttt ccaatatcat ttgctccatc accttcggag aacgctttga
661 gtaccaggat agttggtttc agcagctgct gaagttacta gatgaagtca catacttgga
721 ggcttcaaag acatgccagc tctacaatgt ctttccatgg ataatgaaat cctgcctgg
781 accccaccaa actctcttca gcaactggaa aaaactgaaa ttgtttgttt ctcatatgat
841 tgacaaacac agaaaggatt ggaatcctgc agaaacaaga gactttattg atgcttacct
901 taaagaaatg tcaaagcaca caggcaatcc tacttcaagt ttccatgaag aaaacctcat
961 ctgcagcacc ctggacctct tctttgccgg aaccgagaca acttccacaa ctctgcgatg
1021 ggctctgctt tatatggccc tctacccaga aatccaagaa aaagtacaag ctgagattga
1081 cagagtgatt ggccaggggc agcagccgag cacagccgcc cgggagtcca tgccctacac
1141 caatgctgtc atccatgagg tgcagagaat gggcaacatc atcccctga acgttcccag
1201 ggaagtgaca gttgatacca ctttggctgg gtaccacctg cccaagggta ccatgatcct
1261 gaccaatttg acggcgctgc acagggaccc cacagagtgg ccaccccctg acacattcaa
1321 tccggaccat tttctggaga atggacagtt taagaaaagg gaagccttta tgcctttctc
1381 aataggaaag cgggcatgcc tcggagaaca gttggccagg actgagctgt ttatttctt
1441 ccttcccctt atgcaaaaat ttaccttcag gcccccaaac aatgagaagc tgagcctgaa
1501 gtttagaatg ggtatcacca tttccccagt cagtcaccgc ctctgcgctg ttcctcaggt
1561 gtaatattgt taagaaagaa aggggcaagg aaagtaagaa gacatggcac gtgttctgaa
1621 accactggtg tctgctcaga tgtgttggga caaaatgaaa gtgactttca gaaagatca
1681 gaggaatttg actcagagaa aactagatcc aaatcccagc tctactgtct cgtccgaatt
1741 agccttggga aaatcattta tatgctaaat aatttacctt tttatctagg agatgaaaag
```

SEQ ID NO: 1

Fig. 1

```
1801 aggataatgt tccttccat  aaagaaagtt cttgtaagaa tcaaaagaaa tggtgagctt
1861 taagtggttt gtaaaccata aaacacatca taaaagttct atctataaaa aaaaaaaaaa
1921 aaaaaaaaaa
```

SEQ ID NO.: 1 Continued

→ ITR Region
```
   1 ttggccactc cctctctgcg cgctcgctcg ctcactgagg ccgggcgacc aaaggtcgcc
  61 cgacgcccgg gctttgcccg ggcggcctca gtgagcgagc gagcgcgcag agagggagtg
 121 gccaactcca tcactagggg ttcctggagg ggtggagtcg tgacgtgaat tacgtcatag
```
→ Rep Region
```
 181 ggttagggag gtcctgtatt agaggtcacg tgagtgtttt gcgacatttt gcgacaccat
 241 gtggtcacgc tgggtattta agcccgagtg agcacgcagg gtctccattt tgaagcggga
 301 ggtttaacg cgcagccgcc atgccggggt tttacgagat tgtgattaag gtcccagcg
 361 accttgacgg gcatctgccc ggcatttctg acagctttgt gaactgggtg ccgagaagg
 421 aatgggagtt gccgccagat tctgacatgg atctgaatct gattgagcag gcaccctga
 481 ccgtggccga gaagctgcag cgcgactttc tgacggaatg gcgccgtgtg agtaaggccc
 541 cggaggccct tttctttgtg caatttgaga agggagagag ctacttccac atgcacgtgc
 601 tcgtggaaac caccggggtg aaatccatgg ttttgggacg tttcctgagt cagattcgcg
 661 aaaaactgat tcagagaatt taccgcggga tcgagccgac tttgccaaac tggttcgcgg
 721 tcacaaagac cagaaatggc gccggaggcg ggaacaaggt ggtggatgag tgctacatcc
 781 ccaattactt gctccccaaa acccagcctg agctccagtg ggcgtggact aatatggaac
 841 agtatttaag cgcctgtttg aatctcacgg agcgtaaacg gttggtggcg cagcatctga
 901 cgcacgtgtc gcagacgcag gagcagaaca aagagaatca gaatcccaat tctgatgcgc
 961 cggtgatcag atcaaaaact tcagccaggt acatggagct ggtcgggtgg ctcgtggaca
1021 agggattac ctcggagaag cagtggatcc aggaggacca ggcctcatac atctccttca
1081 atgcggcctc caactcgcgg tcccaaatca aggctgcctt ggacaatgcg ggaaagatta
1141 tgagcctgac taaaaccgcc cccgactacc tggtgggcca gcagcccgtg gaggacattt
1201 ccagcaatcg gatttataaa attttggaac taaacgggta cgatccccaa tatgcggctt
1261 ccgtctttct gggatgggcc acgaaaaagt tcggcaagag gaacaccatc tggctgtttg
1321 ggcctgcaac taccgggaag accaacatcg cggaggccat agcccacact gtgcccttct
1381 acggtgcgt aaactggacc aatgagaact ttccctttcaa cgactgtgtc gacaagatgg
1441 tgatctggtg ggaggagggg aagatgaccg ccaaggtcgt ggagtcggcc aaagccattc
1501 tcggaggaag caaggtgcgc gtggaccaga aatgcaagtc ctcggcccag atagacccga
1561 ctccgtgat cgtcacctcc aacaccaaca tgtgcgccgt gattgacggg aactcaacga
```

SEQ ID NO.: 2

Fig. 3A

```
1621 ccttcgaaca ccagcagccg ttgcaagacc ggatgttcaa atttgaactc acccgccgtc
1681 tggatcatga ctttgggaag gtcaccaagc aggaagtcaa agactttttc cggtgggcaa
1741 aggatcacgt ggttgaggtg gagcatgaat tctacgtcaa aaagggtgga gccaagaaaa
1801 gacccgcccc cagtgacgca gatataagtg agcccaaacg ggtgcgcgag tcagttgcgc
                        Inf Region
1861 agccatcgac gtcagacgcg gaagcttcga tcaactacgc agacaggtac caaaacaaat
1921 gttctcgtca cgtgggcatg aatctgatgc tgtttccctg cagacaatgc gagagaatga
1981 atcagaattc aaatatctgc ttcactcacg gacagaaaga ctgtttagag tgctttcccg
2041 tgtcagaatc tcaacccgtt tctgtcgtca aaaaggcgta tcagaaactg tgctacattc
2101 atcatatcat gggaaaggtg ccagacgctt gcactgcctg cgatctggtc aatgtggatt
2161 tggatgactg catctttgaa caataaatga tttaaatcag gtatggctgc cgatggttat
                                    Lip region
2221 cttccagatt ggctcgagga cactctctct gaaggaataa gacagtggtg gaagctcaaa
2281 cctggcccac caccaccaaa gcccgcagag cggcataagg acgacagcag gggtcttgtg
2341 cttcctgggt acaagtacct cggacccttc aacggactcg acaagggaga gccggtcaac
                                    Cap Region
2401 gaggcagacg ccgcggccct cgagcacgta caaagcctac gaccggcagc tcgacagcgg
2461 agacaacccg tacctcaagt acaaccacgc cgacgcggag tttcaggagc gccttaaaga
2521 agatacgtct tttgggggca acctcggacg agcagtcttc caggcgaaaa agagggttct
2581 tgaacctctg ggcctggttg aggaacctgt taagacggct ccgggaaaaa agaggccggt
2641 agagcactct cctgtggagc cagactcctc ctcgggaacc ggaaaggcgg gccagcagcc
2701 tgcaagaaaa agattgaatt ttggtcagac tggagacgca gactcagtac ctgaccccca
2761 gcctctcgga cagccaccag cagcccctc tggtctggga actaatacga tggctacagg
2821 cagtggcgca ccaatggcag acaataacga gggcgccgac ggagtgggta attcctccgg
2881 aaattggcat tgcgattcca catggatggg cgacagagtc atcaccacca gcacccgaac
2941 ctgggccctg cccacctaca acaaccacct ctacaaacaa atttccagcc aatcaggagc
3001 ctcgaacgac aatcactact ttggctacag cacccttgg gggtattttg acttcaacag
3061 attccactgc cacttttcac cacgtgactg gcaaagactc atcaacaaca actggggatt
3121 ccgacccaag agactcaact tcaagctctt taacattcaa gtcaaagagg tcacgcagaa
```

SEQ ID NO.: 2 Continued

Fig. 3B

```
3181 tgacggtacg acgacgattg ccaataacct taccagcacg gttcaggtgt ttactgactc
3241 ggagtaccag ctcccgtacg tcctcggctc ggcgcatcaa ggatgcctcc cgccgttccc
3301 agcagacgtc ttcatggtgc cacagtatgg atacctcacc ctgaacaacg ggagtcaggc
3361 agtaggacgc tcttcatttt actgcctgga gtactttcct tctcagatgc tgcgtaccgg
3421 aaacaacttt accttcagct cacttttga ggacgttcct ttccacagca gctacgctca
3481 cagccagagt ctggaccgtc tcatgaatcc tctcatcgac cagtacctgt attacttgag
3541 cagaacaaac actccaagtg gaaccaccac gcagtcaagg cttcagtttt ctcaggccgg
3601 agcgagtgac attcgggacc agtctaggaa ctggcttcct ggaccctgtt accgccagca
3661 gcgagtatca agacatctg cggataacaa caacagtgaa tactcgtgga ctggagctac
3721 caagtaccac ctcaatggca gagactctct ggtgaatccg gccatggcaa gccacaagga
3781 cgatgaagaa aagttttttc ctcagagcgg ggttctcatc tttgggaagc aaggctcaga
3841 gaaaacaaat gtgaacattg aaaaggtcat gattacagac gaagaggaaa tcggaacaac
3901 caatcccgtg gctacggagc agtatggttc tgtatctacc aacctccaga gaggcaacag
3961 acaagcagct accgcagatg tcaacacaca aggcgttctt ccaggcatgg tctggcagga
4021 cagagatgtg taccttcagg ggcccatctg ggcaaagatt ccacacacgg acggacattt
4081 tcacccctct cccctcatgg gtggattcgg acttaaacac cctcctccac agattctcat
4141 caagaacacc ccggtacctg cgaatccttc gaccaccttc agtgcggcaa agtttgcttc
4201 cttcatcaca cagtactcca cgggacacgg tcagcgtgga gatcgagtgg gagctgcaga
4261 aggaaaacag caaacgctgg aatcccgaaa ttcagtacac ttccaactac aacaagtctg
4321 ttaatcgtgg acttaccgtg gatactaatg gcgtgtattc agagcctcgc cccattggca
4381 ccagatacct gactcgtaat ctgtaattgc ttgttaatca ataaaccgtt taattcgttt
4441 cagttgaact ttggtctctg cgtatttctt tcttatctag tttccatggc tacgtagata
                                            ──────▶ ITR Region
4501 agtagcatgg cgggttaatc attaactaca aggaaccccct agtgatggag ttggccactc
4561 cctctctgcg cgctcgctcg ctcactgagg ccgggcgacc aaaggtcgcc cgacgcccgg
4621 gctttgcccg ggcggcctca gtgagcgagc gagcgcgcag agagggagtg gccaa
```

SEQ ID NO.: 2 Continued

Fig. 3C

SEQ ID NO: 3

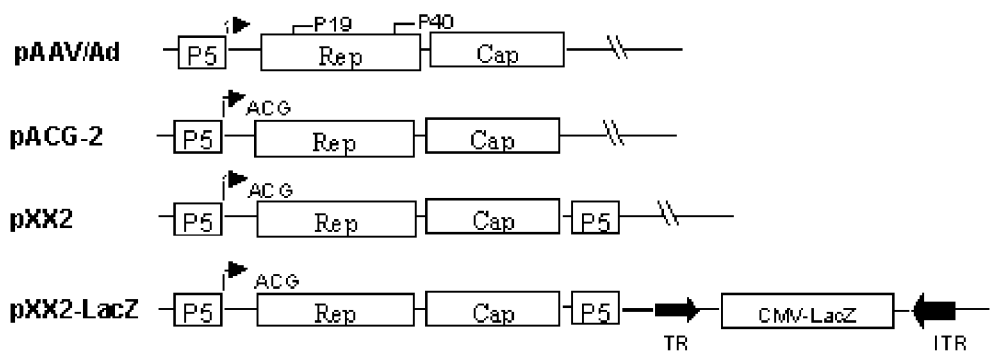
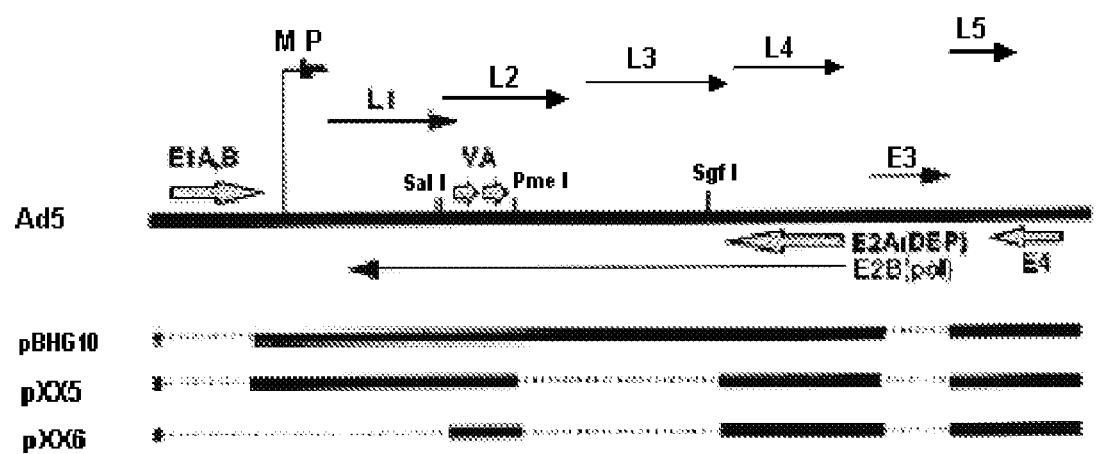
Fig. 8

Growth curve of tumor tissue

Effects of CYP epoxygenase on the invasion of

Fig.5 Epoxygenase inhibitors 17-ODYA inhibit the proliferation of tumor cells

RECOMBINANT ADENO-ASSOCIATED VIRUS EXPRESSING HUMAN ANTISENSE GENE CYP2J2 AND ITS PREPARATION METHODS

FIELD OF THE INVENTION

The invention relates to a construction and preparation method of a recombinant adeno-associated virus expressing antisense human CYP2J2 gene (rAAV-anti2J2), and more specifically to cloning of human CYP2J2 gene, a package and preparation method of the recombinant adeno-associated virus containing the antisense CYP2J2 gene. The invention further relates to a pharmaceutical application of the recombinant adeno-associated virus, a CYP epoxygenase selective inhibitor, and an epoxyeicosatrienoic acid blocker, for the treatment of tumors.

BACKGROUND OF THE INVENTION

With extensive study and understanding of cytochrome P450 (CYP) epoxygenase, attention has been increasingly devoted to its function in physiology and pathophysiology. Especially, the CYP metabolic pathway of arachidonic acid (AA) discovered 20 years ago has been suggested to be focal points in the present research of human biology and pathophysiology. AA-CYP epoxygenase metabolizes arachidonic acid to four different epoxyeicosatrienoic acids (EETs), namely 5,6-, 8,9-, 11, 12-, 14, 15-EETs. CYP epoxygenase consists of two types, 2C and 2J. Some studies have indicated that 2C is widely distributed in organism, particularly abounding in liver and vein. At present, six clones of 2J have been found and only 2J2 is expressed in human, particularly abundant in heart and vascular endothelial cells. It has been found by us and foreign experts that EETs play an important role in the homeostasis regulation of cardiovascular system, for regulation of blood pressure, protection of heart and vascular endothelial cells, and anti-apoptosis. However, our research indicates that epoxygenase gene selectively overexpresses in human tumor tissues, thereby promoting the proliferation and metastases of tumor cells and decreasing the apoptosis of antitumor cells. Thus, the study is extremely important for tumor treatment. Tumor is a frequent and common disease of people in modern society, with bad prognosis and high mortality. Furthermore, it has been a main cause of death in our country and even in the world. It is a multigenic, multistep, and multistage regulated chronic disease and no good treatment effects achieved using conventional drugs. With the development of the theory and technology of molecular biology, particularly the introduction of gene therapy, it is possible to get good results for tumor treatment. However, as an important medical industry in the 21st century, gene therapy exhibits disadvantages, for example, the choice of gene therapy vectors.

For gene therapy for tumor, we have constructed a recombinant adeno-associated virus comprising antisense human CYP2J2 cDNA and obtained high titer virus meeting the requirements for tumor treatment. It has been verified in animal experiments that it can inhibit the growth of tumor cells. So there is a hope of truly meeting the requirements of clinical treatment. In addition, we have studied the function and mechanism of AAV-CYP epoxygenase inhibitor for inhibiting the proliferation of malignant tumor have demonstrated the pharmaceutical applications of AAV-CYP epoxygenase selectively overexpressed in human tumor with CYP epoxygenase inhibitor inhibits the proliferation of malignant tumor.

SUMMARY OF THE INVENTION

Inventors have successfully inserted the CYP2J2 cDNA inversely into the eukaryotic expression vector $pXXUF_1$ to construct a recombinant plasmid $pXXUF_1$-anti2J2. Subsequently, using calcium phosphate precipitation technique, $pXX_2$, $pXX_6$, and $pXXUF_1$-anti2J2 are cotransfected into 293 cell to pack and prepare the recombinant adeno-associated virus expressing antisense human CYP2J2 (rAAV-anti2J2). The virus is purified by heparin column and a titer thereof is measured using dot blot hybridization. Moreover, the obtained recombinant adeno-associated virus is transfected into different kinds of human tumor cell lines and experiments show that the recombinant adeno-associated virus comprising the antisense CYP2J2 gene can significantly inhibit the proliferation and migration of tumor cells and promote the apoptosis thereof. Experiments further show that when cell lines transfected with rAAV-anti2J2 are transported into the subcutaneous tissues of nude mice, the growth of tumor cells therein is significantly inhibited by the rAAV-anti2J2. In addition, a CYP2J2 selective inhibitor also shows the same function, which provides a new idea and direction for developing new medicines for treating tumors.

Thus, it is one objective of the invention to provide a recombinant adeno-associated virus (rAAV) comprising an antisense human CYP2J2 gene.

It is another objective of the invention is to provide a method of packaging and preparation of a recombinant adeno-associated virus comprising an antisense human CYP2J2 gene.

It is further another objective of the invention is to provide an experimental method and a result thereof of inhibiting the proliferation of tumor cells and treating tumor using a CYP epoxygenase selective inhibitor and an EET blocker.

It is still another objective of the invention is to provide a method for treating tumor using a recombinant adeno-associated virus comprising an antisense human CYP2J2 gene.

To achieve the above objectives, in accordance with one embodiment of the invention, there is provided a recombinant adeno-associated virus expressing antisense human CYP2J2 gene and a preparation method thereof. The recombinant adeno-associated virus provided in the invention is prepared through cloning human CYP2J2 cDNA (1509 bp, which encodes the protein containing 503 amino acids) from human leucocyte DNA by PCR, cotransfecting with three plasmids using the calcium phosphate precipitation technique to pack and prepare the recombinant adeno-associated virus containing the antisense target gene, and purifying. The recombinant adeno-associated virus prepared by the above method is transfected into different kinds of human tumor cell lines, thereby significantly inhibiting the proliferation and migration of tumor cells, promoting the apoptosis of tumor cells, and suppressing the growth and metastases of tumor. Therefore, it is proved that a selective inhibitor of CYP2J2 and the recombinant adeno-associated virus expressing human antisense gene CYP2J2 are a potential medicine for treating tumors.

The rAAV expressing antisense human CYP2J2 gene is produced by a method of co-transfection into 293 cell using calcium phosphate precipitation, the rAAV comprising the following three plasmids:

a) $pXX_2$: a packing plasmid comprising a nucleotide sequence encoding AAV Rep and Cap protein, providing the essential Rep protein for rAAV replication, wherein the nucleotide sequence is operably linked upstream and downstream to a p5 promoter respectively to increase expression efficiency 15-fold;

b) $pXXUF_1$: a eukaryotic expression vector comprising a CMV promoter, a multiple cloning site of NotI for insertion of target genes, $pXXUF_1$ linking the CYP epoxygenase gene inversely, and inverted terminal repeats (ITRs), the expression vector responsible for the replication of virus, package of virus capsid, and carrying target genes; and c) $pXX_6$: a helper plasmid deleted of the pathogenic gene sequences of adenovirus and comprising an E1A, an E2A, and a VA1 RNA gene of adenovirus, proteins expressed by the plasmid stimulating the transcription and translation of rAAV gene, thereby ensuring the yield of rAAV.

In accordance with another embodiment of the invention, there is provided a method of preparing a recombinant adeno-associated virus (rAAV) expressing antisense human CYP2J2 gene, comprising steps of:

1) providing a first plasmid $pXX_2$ for virus packaging, comprising a nucleotide sequence encoding AAV Rep and Cap protein, and a second plasmid $pXX_6$ stimulating the transcription and translation of rAAV gene, comprising an E1A, an E2A, and a VA1 RNA gene;

2) providing an eukaryotic expression vector $pXXUF_1$ comprising an AAV genome lacking of sequences coding the Cap and Rep protein, and inserting an antisense human CYP2J2 gene into the $pXXUF_1$ to produce a recombinant plasmid $pXXUF_1$-anti2J2;

3) cotransfecting the $pXX_2$, the $pXX_6$, and the $pXXUF_1$-anti2J2 into 293 cell using calcium phosphate precipitation, recovering the 293 cell, purifying a rAAV therein, and measuring a titer of the rAAV by dot blot hybridization; and 4) transfecting a cancer cell by the rAAV to detect expression and biological activity thereof.

The rAAV is prepared from natural adeno-associated virus using molecular biology methods such as artificial splicing, modification, packing, replication, and purification.

In another aspect, there is provided a pharmaceutical composition comprising the rAAV expressing antisense human CYP2J2 gene and a pharmaceutically acceptable carrier or excipient.

The recombinant adeno-associated virus expressing antisense human CYP2J2 gene of the invention can selectively inhibit the expression of CYP2J2 gene in tumor tissues and treat malignant tumors by inhibiting the synthesis of epoxyeicosatrienoic acids. Selective inhibitors of CYP epoxygenase and antagonists of epoxyeicosatrienoic acids which is a CYP metabolic product of arachidonic acid can selectively inhibit the activity of CYP epoxygenase or block the function of epoxyeicosatrienoic acids, thereby inhibiting the tumor proliferation. All these cause no toxicity to cells.

The recombinant adeno-associated virus expressing antisense human CYP2J2 gene is conserved in China Center for Type Culture Collection(CCTCC), Wuhan University, China, with deposition Date: 30 Jun. 2004, deposited under NO(C-CTCC No): V200411 and systematic nomenclature: recombinant adeno-associated virus expressing antisense human cytochrome P4502J2 gene.

The invention is further described in detail.

To acquire the human CYP2J2 gene, the inventor designs specific primers to amplify CYP2J2 cDNA fragments according to CYP2J2 nucleotide sequences reported in the GeneBank. Genomic DNA is isolated from human leucocyte using phenol-chloroform extraction and used as a template for PCR (Takara PCR kit, Japan; PCR device, Techne, UK). The product is joined inversely to the $pXXUF_1$ to construct a recombinant vector $pXXUF_1$-anti2J2. The recombinant vector is further introduced into host cells, namely E. coli, and thus positive clones is obtained.

The package of recombinant adeno-associated virus requires three plasmids as follows: (1) $pXX_2$: a packing plasmid carrying sequences encoding adeno-associated virus Rep and Cap protein, a p5 promoter is inserted into the upstream and downstream thereof, respectively, thereby improving the expression efficiency by 15-fold; (2) $pXX_6$: a helper plasmid deleting the pathogenic gene sequences of adenovirus and preserving E1A, E2A and VA1 RNA genes of adenovirus. The expressed proteins stimulate the transcription and translation of rAAV gene, so that the yield of rAAV can be ensured; and (3) $pXXUF_1$-anti2J2: a eukaryotic expression vector with human CYP2J2 joined inversely, which contains a CMV promoter with strong expression efficiency and inverted terminal repeats (ITRs) that are essential for the expression of rAAV. The vector is responsible for replication of virus, package of virus capsid, and carries target genes. A mixture of $pXX_2$, $pXX_6$, and $pXXUF_1$-anti2J2 (molar ratio is 1:1:1) is co-transfected into 293 cell using calcium phosphate precipitation. 48-72 h later, the 293 cell is collected, frozen and thawed thrice, and thus the virus is released into the supernatant. The virus is then purified by heparin column, and the titer thereof is measured using dot blot hybridization. Thus, the recombinant adeno-associated virus containing the antisense human 2J2 gene is obtained.

To verify the function of CYP epoxygenase in the generation and development of tumor and the therapeutic action of a CYP epoxygenase selective inhibitor and the recombinant adeno-associated virus containing the antisense 2J2 gene against the tumor, we have studied the highly selective expression of CYP epoxygenase in human tumor tissues and prove that the rAAV-anti2J2 can significantly decrease the expression of 2J2 in tumor cells. Transfection of antisense CYP epoxygenase gene (rAAV-anti2J2), as well as application of a CYP epoxygenase inhibitor (for example, 17-ODYA), can significantly suppress the proliferation of tumor cells, which is below 50% of basal state (P<0.01). On the contrary, transfection of rAAV-CYP2J2 can significantly promote the proliferation of tumor cells and the number of proliferating cells is 2-3 folds higher than that at basal state, namely rAAV-GFP-transfected and nontranfected cells. Likewise, to partially simulate the growth process of tumor cells in human body, rAAV-anti2J2 is transfected into human tongue squamous cell carcinoma cell line, i.e., Tca-8113, and then the transfected cells are transplanted into the subcutaneous tissues of nude mice. The size of tumor is measured and the growth curve of tumor volume is drawn. Studies show that transfection of rAAV-anti2J2 significantly inhibits the growth of tumor.

In addition, it is found through measuring the microvessel density of tumor tissues that transfection of rAAV-anti2J2 significantly decreases the microvessel density of tumor.

Similarly, transfection of rAAV-anti2J2 can significantly inhibit the migration of tumor cells and promote the apoptosis of tumor cells.

The results mentioned above show rAAV-anti2J2 and CYP epoxygenase inhibitor (17-ODYA) can inhibit the proliferation and migration of tumor and promote the apoptosis of tumor cells, so they can be used for tumor treatment. The recombinant adeno-associated virus expressing antisense human CYP2J2 gene (rAAV-anti2J2), which is expressed for a long term in organisms, blocks the transcription and translation of CYP2J2 gene in gene level and decreases the expression of CYP2J2. The effect is more powerful. The clinical application of the recombinant adeno-associated virus expressing antisense human CYP2J2 gene (rAAV-anti2J2) and the epoxygenase inhibitor will play an important role for the treatment of diseases, for example, tumors.

Advantages of the invention are summarized below. The recombinant adeno-associated virus has overcome the disadvantages that other gene expression vectors cannot overcome, and the carried target gene can be transfected into cells in division stage and non-division stage (that is to say, with wide range of transgenosis) with no immunogenicities and high infection efficiency. Furthermore, the target genes can be expressed in vivo for a long term and no adenovirus pollution occurs even replication in large scale in vitro.

BRIEF DESCPIPTION OF THE DRAWINGS

The invention is described hereinbelow with reference to accompanying drawings, in which:

FIGS. 3A-3C shows the nucleotide sequences and detailed regions of adeno-associated virus; FIG. 3B is a continuation of FIG. 3A, and FIG. 3C is a continuation of FIG. 3B;

FIG. 8 shows structural map of plasmid pXX$_2$ and pXX6;

Figure 10A:
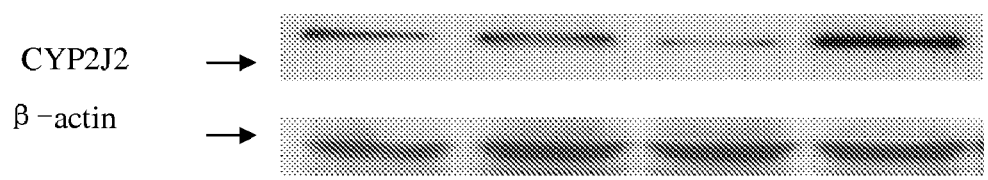
Figure 11:
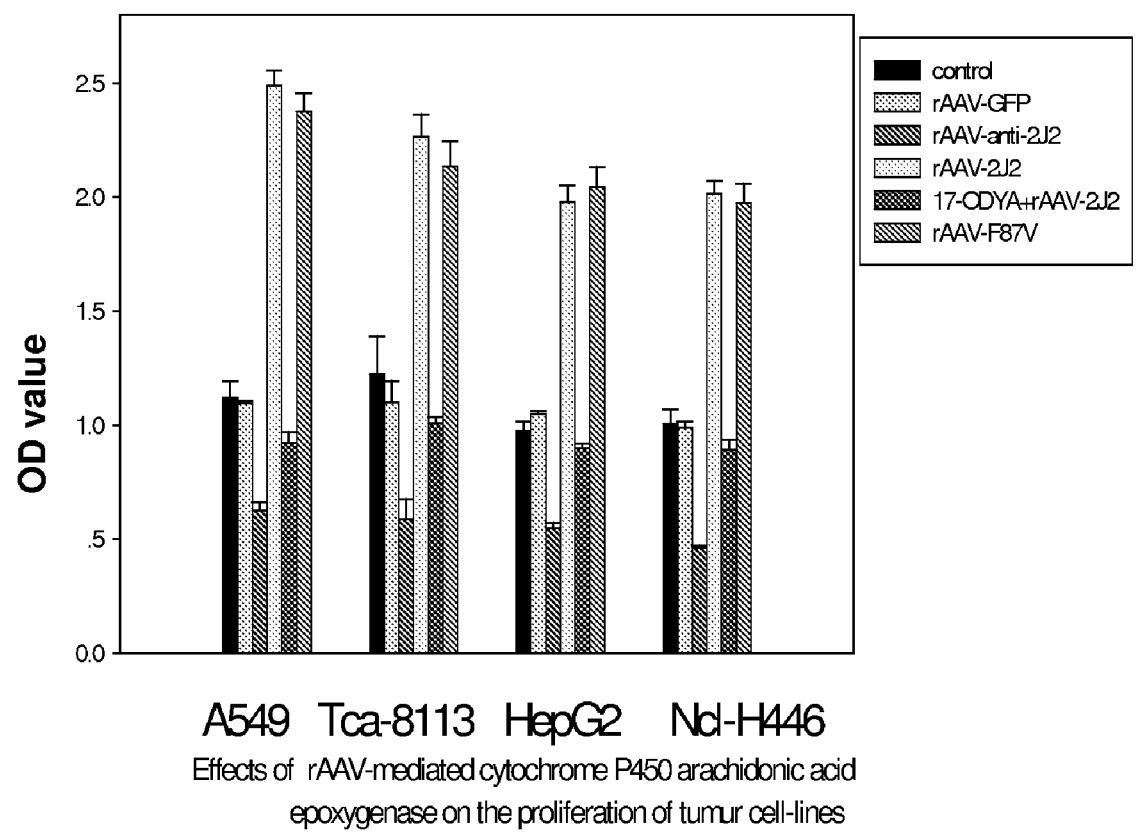
Figure 12:
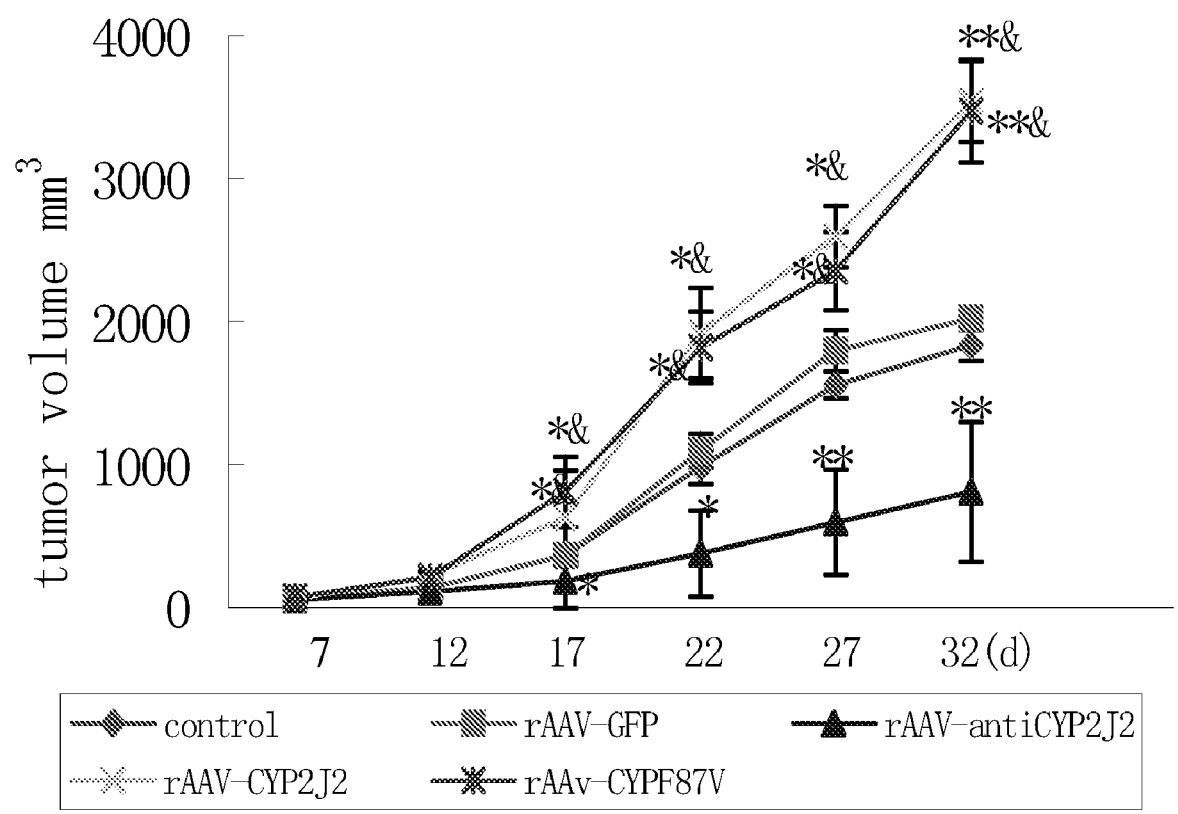
Figure 13:
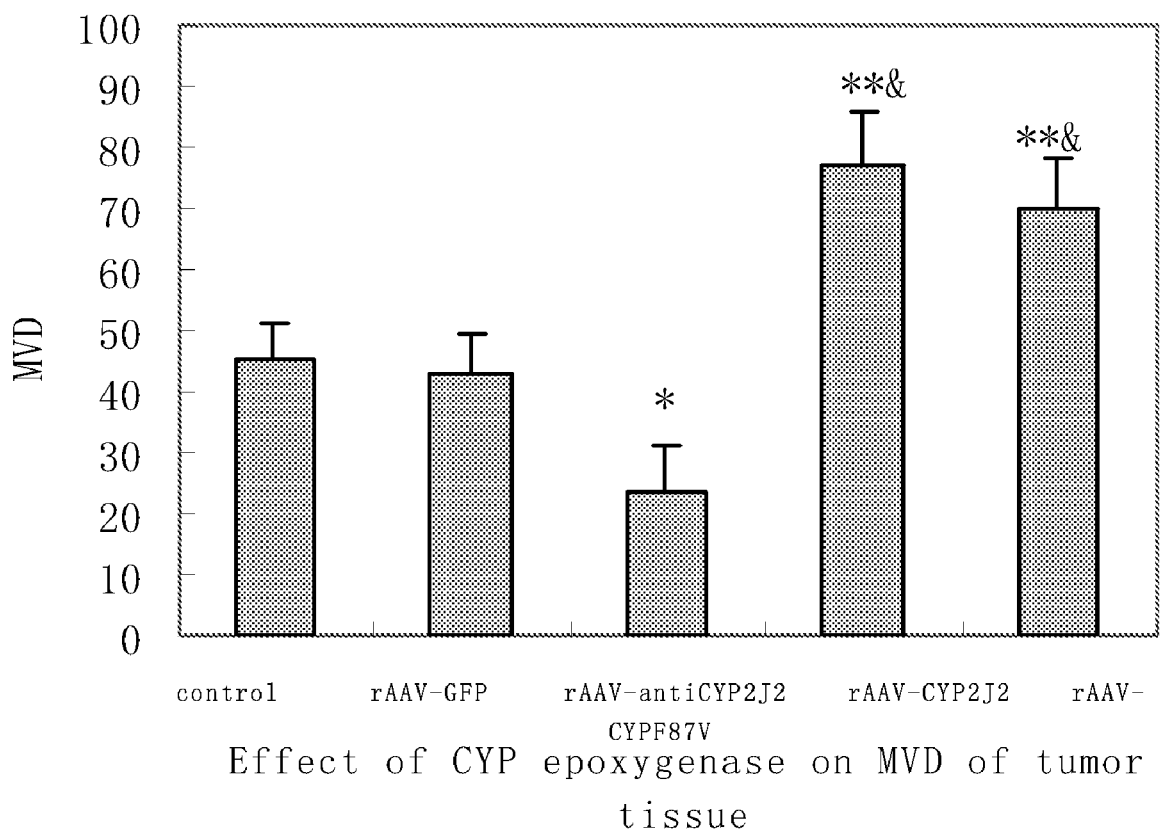
Figure 14A:
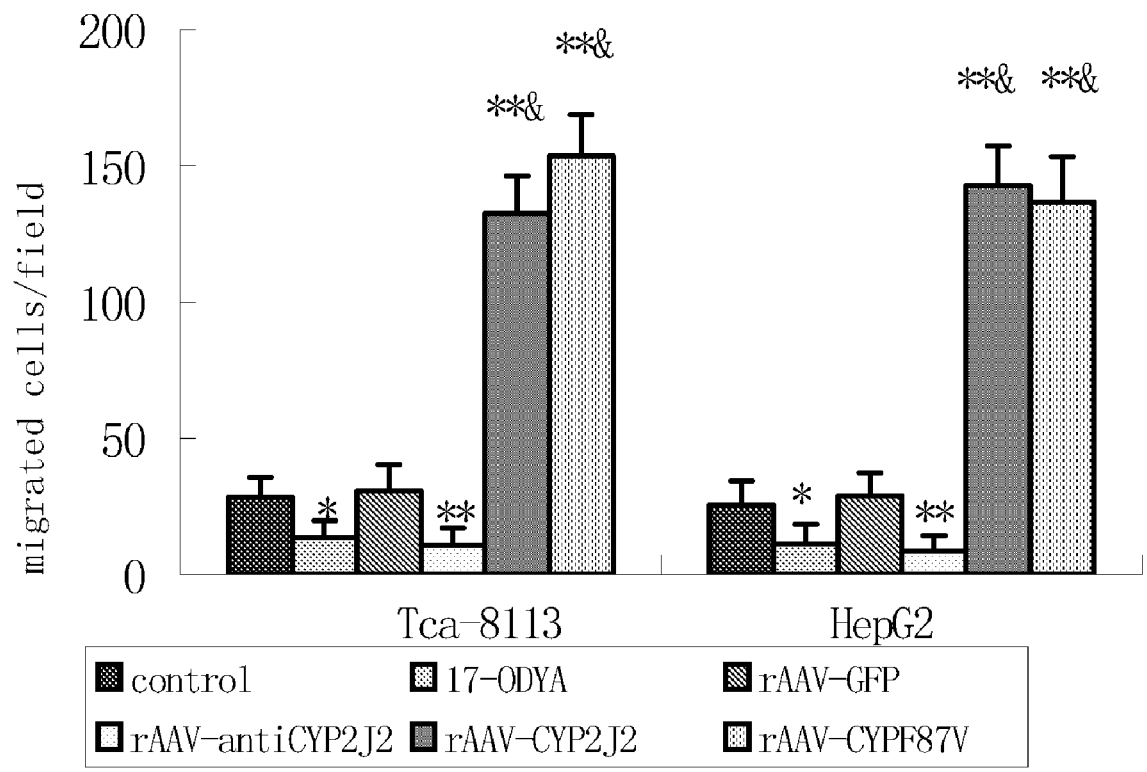
Figure 14B:
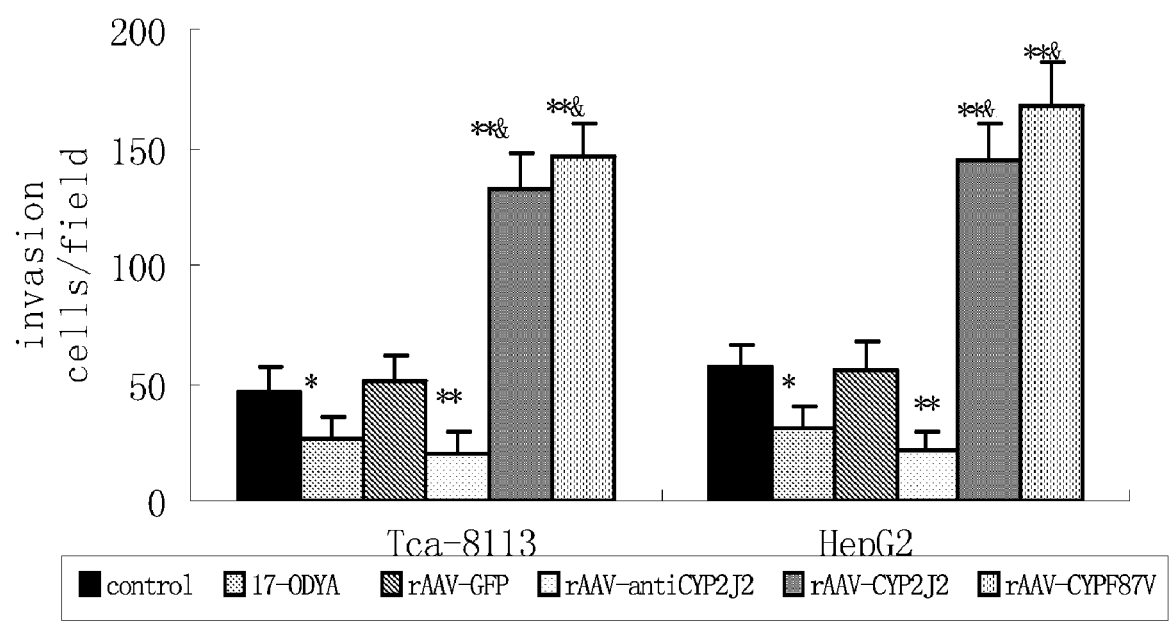
Figure 15:
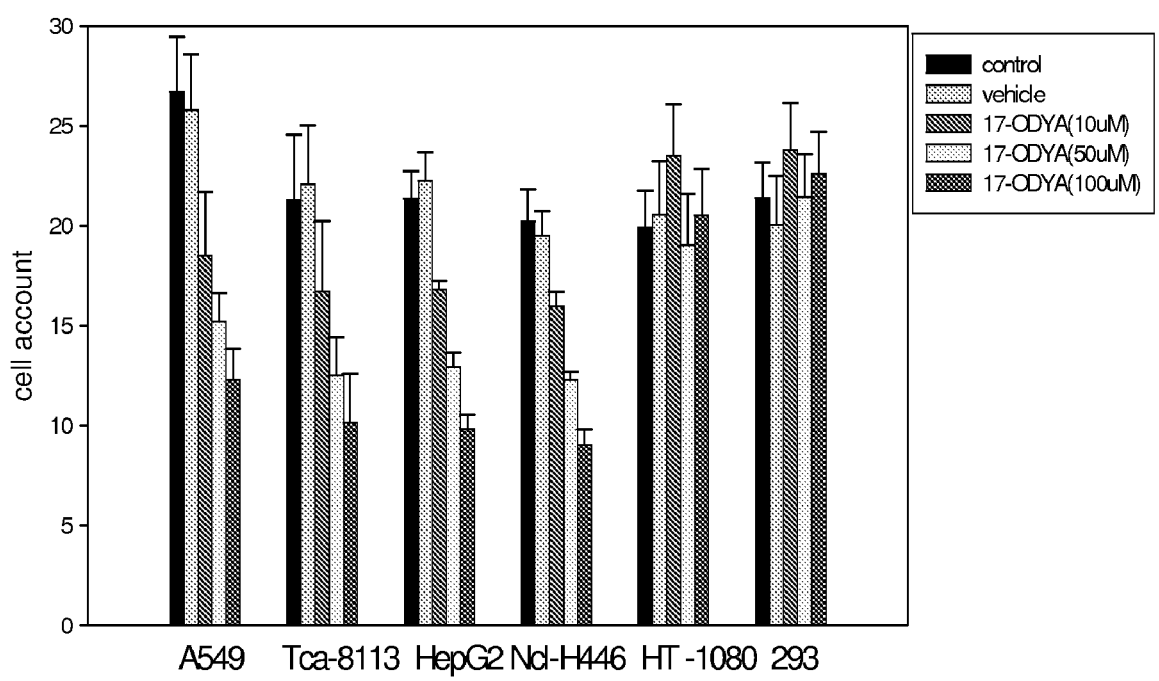
Figure 16:
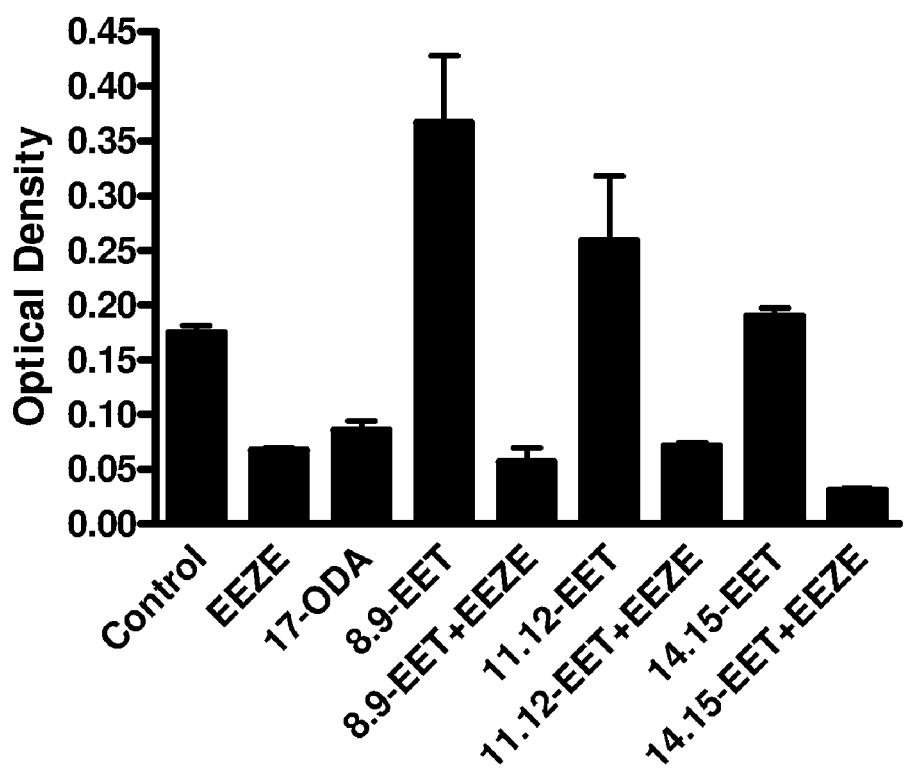
Figure 17:
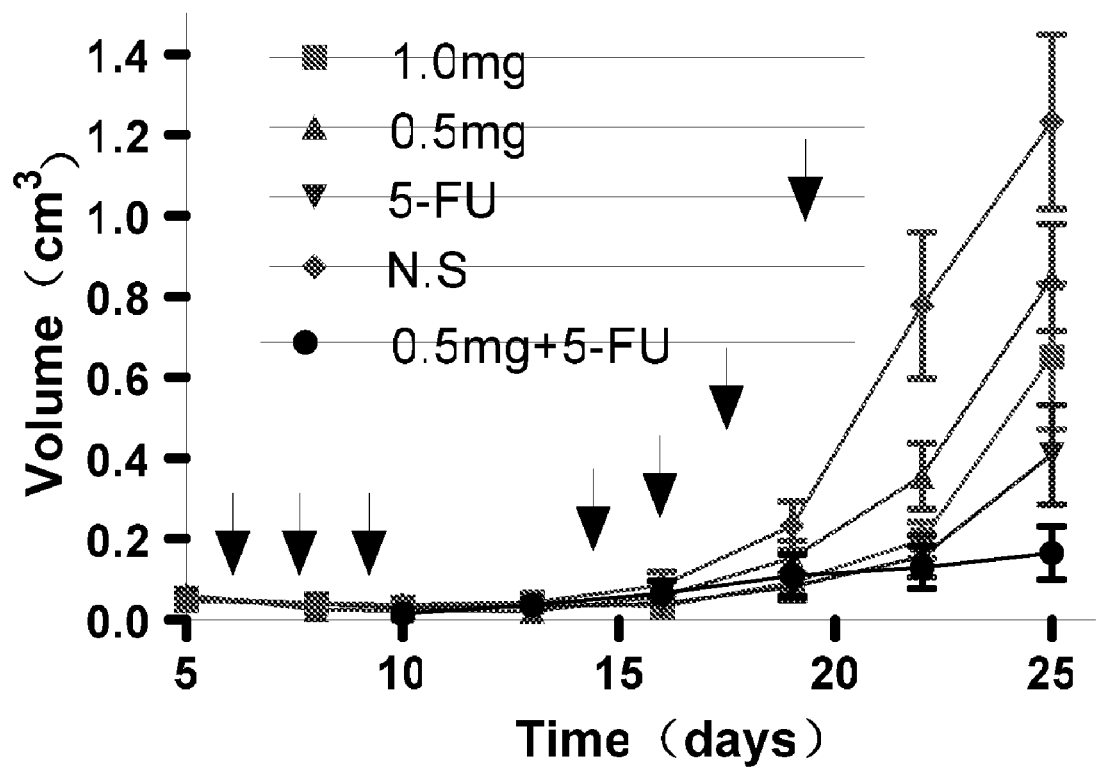

FIG. 10A and FIG. 10B show the effective expression of transfected CYP epoxygenase gene (rAAV-2J2) and that transfected antisense gene (rAAV-anti2J2) can significantly inhibit the expression of CYP2J2 in tumor cells. In FIG. 10A, the effective expression of transfected CYP epoxygenase gene (rAAV-2J2) and the transfected antisense gene (rAAV-anti2J2) can significantly inhibit the expression of CYP2J2 in tumor cells. FIG. 10A: Result of CYP-2J2 Western Blot of proteins extracted from transplantation tumor tissues 32 days after the proceed by which rAAV-2J2 and rAAV-anti2J2 are transfected respectively into tumor cells, which are then transplanted to the subcutaneous tissues of nude mice to form transplantation tumor. FIG. 10B: Result of CYP-2J2 Western Blot of proteins extracted directly from tumor cells that rAAV-2J2 and rAAV-anti2J2 are respectively transfected into. Both the two results show that transfected rAAV-2J2 can express effectively in tumor cells, but transfected rAAV-anti2J2 can significantly inhibit or block the expression of CYP2J2, which are closely related to the fact that CYP2J2 can result in malignant proliferation of tumor and rAAV-anti2J2 can inhibit malignant proliferation of tumor;

FIG. 11 shows the CYP epoxygenase has an effect on proliferation of four tumor cell lines;

FIG. 12 shows the growth curve of transgenic tumor;

FIG. 13 shows the result of microvessel density in transgenic tumor tissues;

FIG. 14 shows the CYP epoxygenase has an effect on invasive ability of tumor cells;

FIG. 15 shows the CYP epoxygenase inhibitor (17-ODYA) dose-dependently inhibits the growth of tumor cells;

FIG. 16 shows the EET blocker 14, 15-EET (100 nmol/L) can inhibit the growth of tumor; and FIG. 17 shows the epoxygenase inhibitor 17-ODYA can inhibit the growth of transplantation tumor without joint use of 5-fluorouracil.

DETAILED DESCRIPTION OF THE INVENTION

Example 1

Cloning of CYP2J2 cDNA and Preparation of a Recombinant Plasmid pXXUF$_1$-anti2J2

Figures 1, 2:
FIG. 1 shows 2J2 sequences (from GeneBank) with a sequence of cDNA open reading frame light-colored.
FIG. 2 shows the construction of plasmid pXXUF$_1$-anti2J2.
Figure 4:
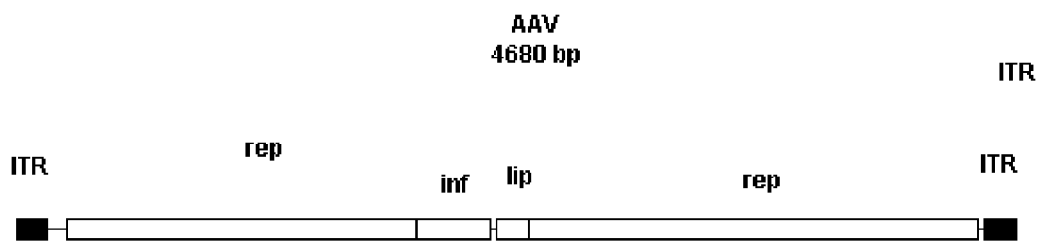
FIG. 4 shows the structure diagram of adeno-associated virus genome.

To clone human CYP2J2 cDNA, PCR primers for amplifying CYP2J2 cDNA according to public CYP2J2 gene sequences (FIG. 1) are designed as follows, upstream primer 5'-GCCCGGAATTCAAAATGATTCTCAAC-3' (SEQ ID NO: 4) and downstream primer 5'-GG CGCA-CAAGCTTTCAAATAAGAGTATAAC-3' (SEQ ID NO: 5) which are synthesized by Wuhan Biosynthesis Company. Genomic DNA is isolated from human leucocyte using phenol-chloroform extraction and used as a template for PCR (Takara PCR kit, Japan; PCR device, Techne, UK). The product is joined inversely to pXXUF$_1$ to construct a recombinant vector pXXUF$_1$-anti2J2 as shown in FIG. 2.

Example 2

Package, Recovery, and Purification of the Recombinant Virus rAAV-anti2J2

I) Features of natural adeno-associated virus (AAV) and recombinant adeno-associated virus (rAAV):

Adeno-associated virus is an animal single strand DNA virus, belonging to family Parvoviridae, subfamily Parvovirinae, genus *Dependovirus*, and is naturally defective, non-enveloped, and non-pathogenic.

Figure 5:
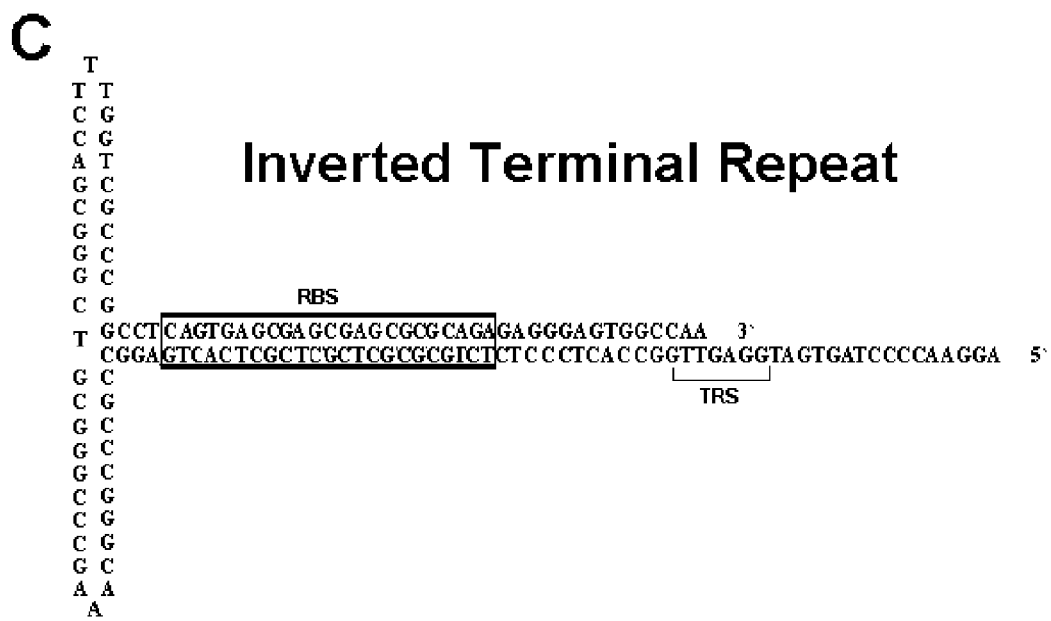
FIG. 5 shows ITR sequences of adeno-associated virus and their secondary structure diagram.
Figure 6:
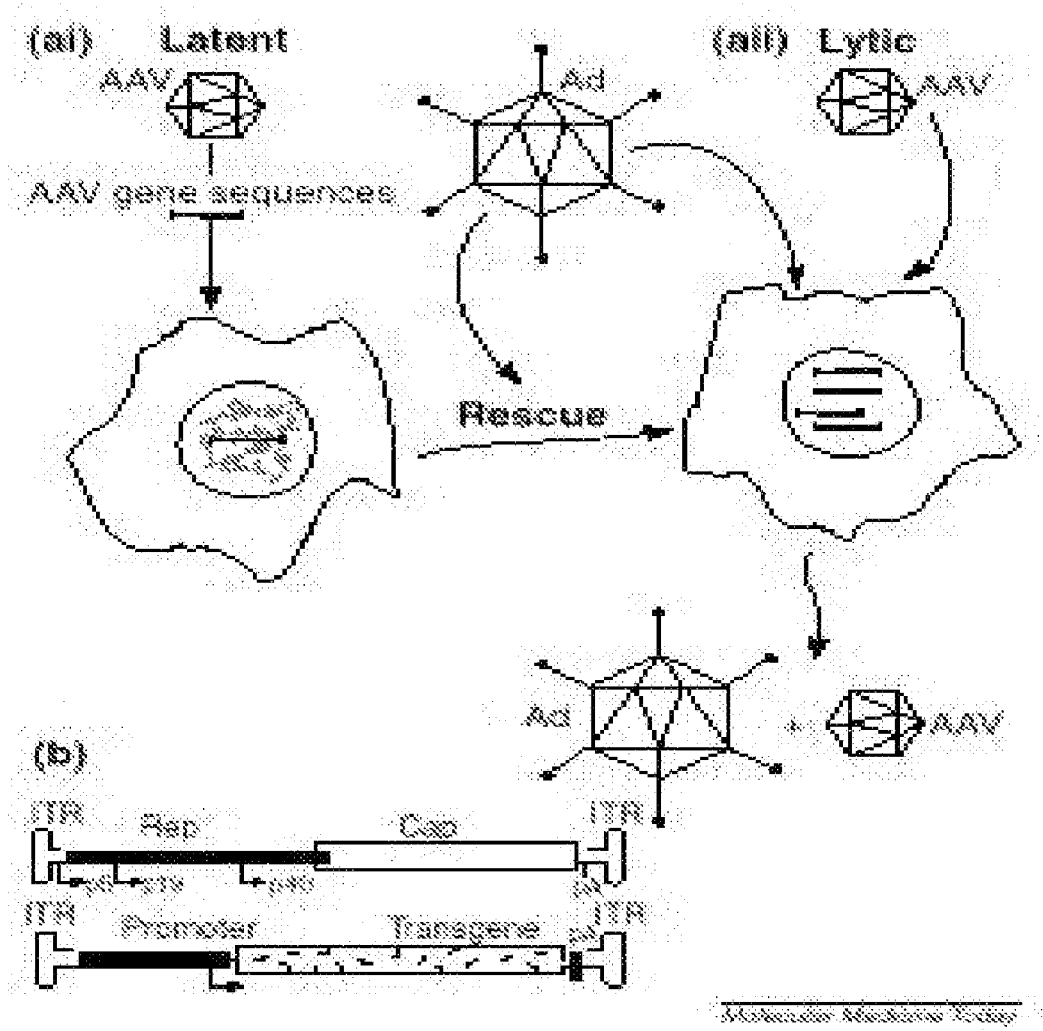
FIG. 6 shows the transcription and translation of adeno-associated virus (part 1)

1. AAV genome is a linear single-stranded DNA comprising 4680 nucleotides (sequences as shown in FIGS. 3A-3C), characterized in that:

1) The genome comprises 4 open reading frames (ORF): rep, lip, inf and cap (as shown in FIGS. 3A-3C and FIG. 4). On the left side of the genome DNA, there is a big ORF inhibiting DNA replication due to frame shift mutation or deletion. So it is called rep. The big ORF called cap on the right side encodes three capsid proteins. Other two small ORFs locate in the middle of genome DNA called inf and lip, whose function is not explicit;

2) There are 145 inverted terminal repeat (ITR) sequences at both ends of the DNA strand (as shown in FIGS. 3A-3C). The ITRs form a hairpin structure which is indispensable for initial replication of DNA and package of rAAV genome to form infective virus particles (as shown in FIG. 5);

3) The replication and transcriptional regulation of the adeno-associated virus are quite complicated, which is divided into two kinds of expression patterns according to whether or not there is cotransfecetion of helper virus. The two kinds of expression patterns are proliferative expression and latent expression (as shown in FIG. 6).

Figure 7:
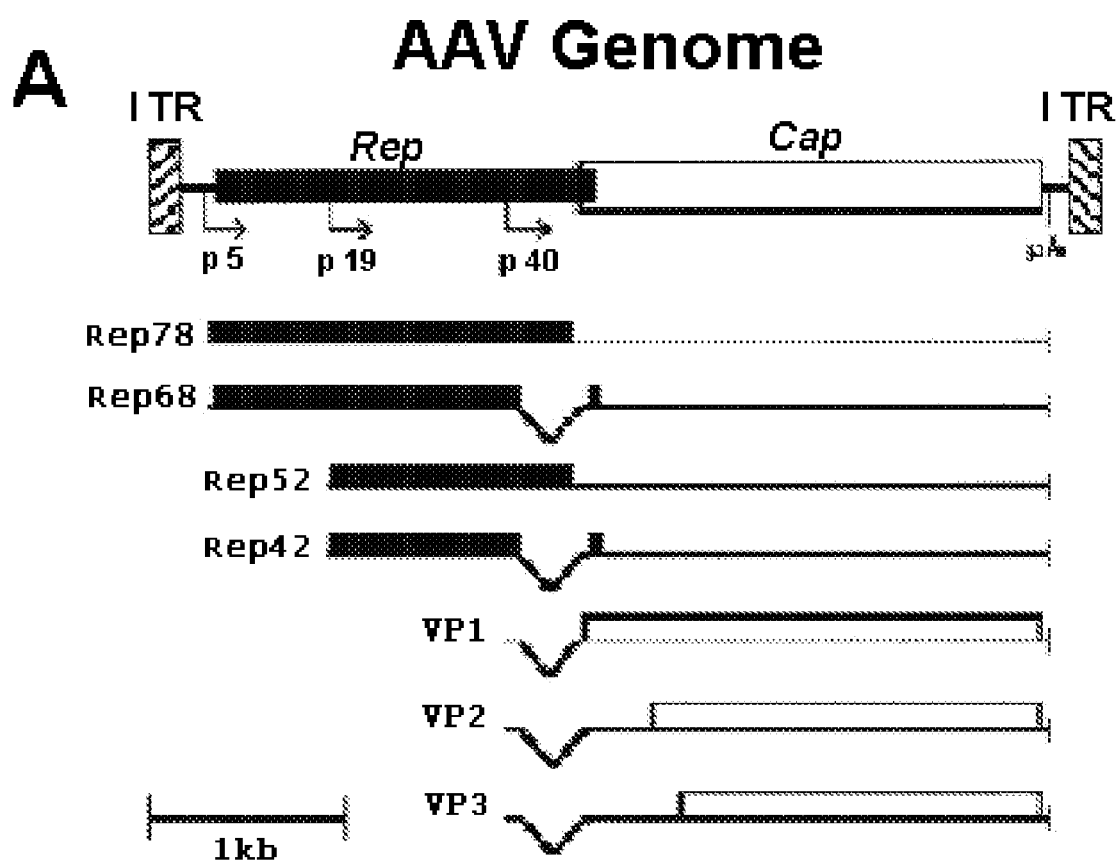
FIG. 7 shows the transcription and translation of adeno-associated virus (part 2)

During the proliferative expression of AAV, 6 kinds of mRNA are transcribed, which are initiated by P5, P19, and P40 promoter respectively, as shown in FIG. 7. During the cotransfection of adenovirus (Ad), the E1A gene of Ad is responsible for trans-activating expression of AAV genes, and the E2A gene of Ad encodes a single strand DNA binding protein, which stimulates the AAV promoter to promote transcription and helps transport AAV from intranucleus to cytoplasm after transcription. In addition, the VA1 RNA of Ad can probably be favorable to the initiation of translation of AAV proteins and AAV can regulate the expression of self genes and helper virus genes positively and negatively. Rep gene of AAV can positively and negatively regulate P5, P19 and P40 promoter to initiate transcription. While Ad exists, the products of rep gene perform positive regulation, and without cotransfection of helper virus, the products of rep gene do negative regulation.

Without helper virus, DNA of AAV can be integrated into the host cell genome in the form of double strands and persist in latent form for latent infection of AAV. The specific site of integration of AAV locates in the 19q13.3-19q ter of human chromosome. Besides negative regulation of rep gene products, they also recognize and bind the specific site of integration, i.e., GGTG sequence, and mediate the recombination (recombination) between ITR and integrating site. The infection of adenovirus can promote AAV to be proliferative and infected.

2. AAV is used as a vector for gene therapy

Figure 9:
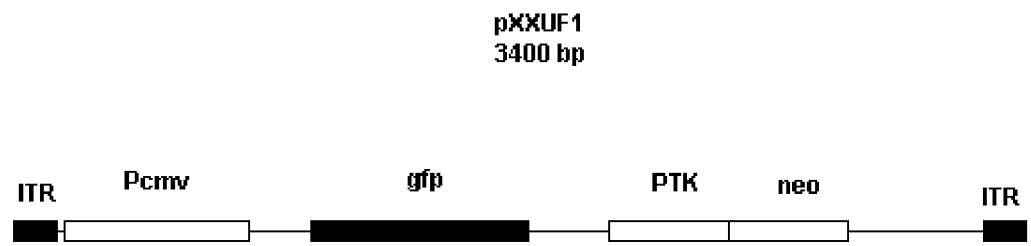
FIG. 9 shows the construction of plasmid pXXUF1 (the map only shows the main regions of plasmid. Actually the two plasmids have already been converted to a 5000-7000 bp cyclic structure, but other parts are unshown for insignificance)

As far as we know, AAV is a unique eukaryote cell virus integrating into the specific site of chromosome of host genome. This offers a new hope for gene therapy. Compared with nonintegrated vectors, the AAV vector not only expresses the transgenosis more constantly and stably, but also decreases the insertional mutation rate theoretically resulting from random integration of transgenosis. The vector system we used is obtained through a series of splicing and modification of natural recombinant adeno-associated virus and adenovirus by molecular biology methods, preserving essential parts for replication and transcription of recombinant adeno-associated virus and auxiliary parts of adenovirus late genes and deleting all unnecessary parts, thus, one one hand making latent infection of virus stable for a long time, on the other hand, avoiding pathogenic danger from adenovirus. Moreover, the expression of late genes of adenovirus can ensure the expression efficiency of cloned gene. The vector system comprises as follows:

$pXX_2$ (FIG. 8): comprising cap and rep genes of AAV (pAGG-2 is obtained now) and a p5 promoter inserted into an appropriate position of the downstream of pACG-2(the original position is cute off with XbaI and PstI and joined to the appropriate position of pACG-2);

$pXX_6$ (FIG. 8): a 8 kb fragment is cut off from an adenovirus re-bult plasmid pBH10 (E1, E3 gene and packaging signal have been deleted) using PmeI and SgfI to yield $pXX_5$, coding regions of E2A, E4 and VA of pXX5 are cut off using ClaI and SalI and cloned in pBS;

$pXXUF_1$ (FIG. 9): plasmid $pXXUF_1$ for package of rAAV comprising gfp gene driven by the CMV promoter (as shown by arrow), gfp gene being introduced into the NotI site after deleting all the encoding genes of recombinant adeno-associated virus, and converted to a circle which is easy for gene cloning and expression.

II) Package and recovery of recombinant virus rAAV-anti2J2

Plasmid $pXX_2$, $pXX_6$, and $pXXUF_1$-anti2J2 are extracted and purified using DNA Purification System (Promega). The preparation method follows the instructions.

293 cells (human neuroblastoma cell lines) are transferred into several 150 mm culture plates. The culture medium involved therein comprises 0.25% trypsin, high sugar DMEM media, and neonatal bovine serum (Gibco). When cells grow to 60%-70% of crowding level, plasmids $pXX_2$, $pXX_6$, and $pXXUF_1$-anti2J2 (molar ratio 1:1:1, mass ratio 1.7:3.8:1) are co-transfected into 293 cell based on 85 μg DNA per 150 mm culture plate using calcium phosphate precipitation method. First, plasmids $pXX_2$, $pXX_6$, and $pXXUF_1$-anti2J2 are respectively added to a 250 mL sterile culture flask, followed by addition of 2.5 M $CaCl_2$ (160 μL per plate), sterile deionized water, and 2×BBS (pH6.95, 1.6 mL per plate). The mixture is shaken and small calcium phosphate particles form. The mixture is incubated at room temperature for 30 min. The culture medium in the culture plate is aspirated and discarded. 3 mL DNA-calcium phosphate complexes are added. The mixture is cultured at 35° C. at 3% $CO_2$ for 16-24 h, and then the culture media is updated. The mixture is further cultured at 37° C. at 3% $CO_2$ for 36-48 h. 48-72 h later after transfection, the culture media is aspirated and discarded, a small amount of PBS buffer added, the 293 cells in the plate are collected, and stored at −80° C.

The 293 cells are purified using heparin column to remove allotype proteins therein. The method is described below. The collected 293 cells transfected with virus are frozen and thawed thrice, 0.1 mg DNase I and 0.1 mg RNase A added, and then the mixture is incubated at 37° C. for 2 h, followed by addition of 0.5% deoxycholic acid. The mixture is further incubated at 37° C. for 30 min, and then centrifuged for several minutes. The supernatant is filtered using 5 μm and 0.8 μm filter membranes. 8 mL of a heparin agarose suspension is added into a glass column (2.5 cm in diameter) with a valve. After the agarose suspension drains away, a filter membrane is disposed on the formed agarose bed. The bed is balanced using 25 mL of PBS (pH7.4). The valve is closed, and the above-mentioned virus is added to the glass column. The valve is opened, and the virus drips at a controlled speed of 1 drop per second. After the virus drips off, the column is washed twice using 25 mL of PBS (pH7.4) plus 0.1M NaCl. The virus is washed using 15 mL of PBS (pH7.4) plus 0.4M NaCl and concentrated using a Millipore Biomax-100K NMWL filter device (UFV2BHK40) to 3-5 mL.

Example 3

Measurement of rAAV-anti2J2 Virus Titer Using Dot Blot Hybridization (1) Labeling and Purification of CYP2J2 cDNA Probe Isotope-labeled nucleotide $\alpha$-$P^{32}$ is purchased from Beijing Yahui Co. Ltd. CYP2J2 fragment is cut off from pXXUF1-anti2J2 using Not I and used as a probe of a target sequence. CYP2J2 fragment is labeled by random prime method and purified. The kits are purchased from Qiagen Co. Ltd. and operation method follows the instructions.

(2) Material Recovery and Preparation of Quantitative Criteria

Recovered materials are treated with appropriate DNase I and RNase A to digest DNA and RNA of cell genome and with proteinase K to digest the virus capsid (all reagents mentioned above are from Takara Co. Ltd., Japan). The mixture is extracted with phenol: chloroform: isoamyl alcohol (25:24:1) to remove precipitates and the virus DNA exists in the supernatant. The supernatant is diluted according to volume ratio. As a standard substance, the target gene fragment, namely CYP2J2 fragment, is double diluted according to molecular amount and treated through heating and alkali denaturation.

(3) Hybridization and Radioautography

A device of dot blot hybridization is placed and a 0.45 μm nylon membrane is disposed thereon according to the size of device. The virus samples to be tested and standard samples are loaded according to volume gradient and molecular gradient, respectively. Subsequently, the membrane is toasted at 80° C. for 2 h and then at 42° C. for 1 h for prehybridization (prehybridization solution is purchased from INTERGRN Co. Ltd). A labeled probe that has been heated is added for hybridization at 45° C. for 12-16 h. The membrane is washed and radioautograph is carried out at −80° C. for 2-3 days. The titer of the prepared rAAVtiter reaches $1 \times 10^{11}$ p.f.u. and can be used for animal experiments.

Example 4

Figure 10:
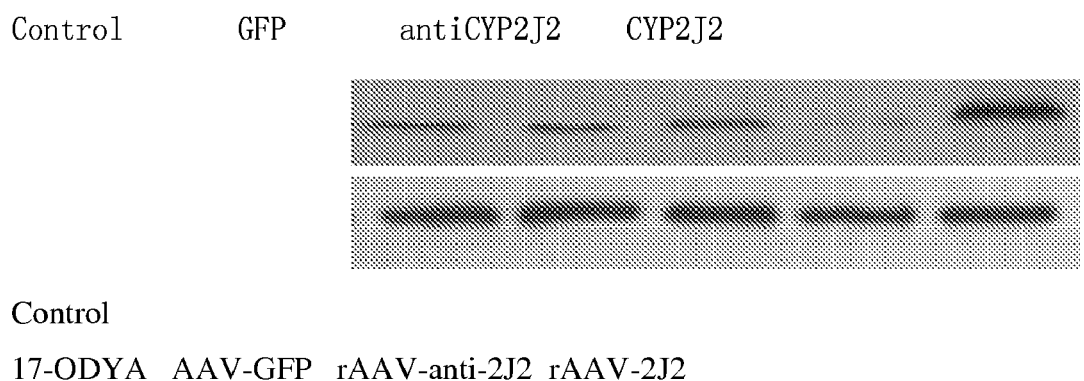

Influence of CYP Epoxygenase on the Growth and Erosion of Tumor (1) Effective Expression of Transfected CYP Epoxygenase Gene in Subcutaneous Transplantation Tumor and Tumor Cell Lines Tissue proteins of subcutaneous transplantation tumor of nude mice and of tumor cell lines, from a control group and rAAV-GFP, rAAV-anti2J2, rAAV-CYP2J2-transfected groups, are extracted, respectively. The expression of epoxygenase in the tissues is determined using western blot. The results show the expression in the transfected rAAV-anti2J2 group decreases significantly compared with the control group and there is no marked difference between the transfected rAAV-GFP group and the control group. The results are shown in FIGS. 10 A and B.

(2) Influence of CYP Epoxygenase and an Inhibitor Thereof on Proliferation of Four Kinds of Tumor Cells In Vitro rAAV-CYP2J2 and rAAV-CYPF87V are transfected into tumor cells so that the epoxygenase is overexpressed therein. The epoxygenase metabolizes arachidonic acid to yield endogenous epoxyeicosatrienoic acids. Thus, the EETs concentration is increased indirectly. This can directly verity that the function of CYP epoxygenase for promoting proliferation of tumor cells. Compared with the control group, transfected rAAV-CYP2J2 and rAAV-CYPF87V can significantly promote the proliferation of tumor cells and the number of proliferating cells is 2-3 fold higher than that in basal state ($P<0.01$). Transfection of antisense CYP epoxygenase gene (rAAV-anti2J2), as well as the application of the CYP epoxygenase inhibitor (17-ODYA), significantly inhibits the proliferation of tumor cells, which is below 50% of basal state ($P<0.01$) (as shown in FIG. 11).

(3) Influence of rAAV-antiCYP Epoxygenase on the Growth of Transplantation Tumor of Nude Mice with Human Tongue Squamous Cell Carcinoma Cell Line In vitro, we have transfected rAAV-anti2J2 into human tongue squamous cell carcinoma cell line Tca-8113 and then transplanted it to the subcutaneous tissues of nude mice to simulate partially the process of growth of tumor cells. On the 7th, 12th, 17th, 22nd, $27^{th}$, and 32nd day after subcutaneous inoculating, maximal diameter (a) and minimum diameter (b) are measured accurately using a vernier caliper. The volume of tumor was calculated as follows: $V=\pi ab^2/6$. The growth curve of tumor volume was drawn. The results show that, after inoculating Tca-8113 to nude mice, experiencing a latent phase of 4-7 days, subcutaneous tumor nodes can be observed by naked eyes and then grow rapidly. The growth cure of transplantation tumor in each group appeared an S-shape with the peak of growth on the 12nd-22nd day. As time went on, the volume of transplantation tumor in each group turned significantly different. The growth in the transfected rAAV-antiCYP2J2 group was delayed and the growth curve appears S-shape by a right shift. On the 32nd day of transfecting rAAV-anti2J2, the volume of tumor was two times larger than that in the basal state. So, CYP epoxygenase can significantly promote the growth of tumor in vivo and, if CYP epoxygenase gene expression is inhibited, the growth of tumor is also inhibited, as shown in FIG. 12.

(4) Influence of rAAV-AS-CYP Epoxygenase on Microvessel Density of Tumor Tissues Animals were killed on the 32nd days after inoculating. The tumor was collected and used to prepare the paraffin section. The microvessel density (MVD) was calculated. Using microscopic observation, microvessels were mainly distributed in mesenchymal cells and peripheral areas of tumors, and seldom inside the tumor tissues. Microvessels increase in the transfected rAAV-CYP2J2 and rAAV-CYPF87V groups and the density thereof was greater (76.8±9.1 and 70.2±7.8) in high power field than that in the control group (42.8±6.4) ($P<0.01$). Microvessels in transfected rAAV-anti2J2 group (23.6±7.3), compared with the control group and transfected rAAV-CYP2J2 group, decreased significantly ($P<0.05$ and $P<0.01$) as shown in FIG. 13.

(5) Influence of rAAV-anti2J2 Epoxygenase on the Migration and Invasion of Tumor Cells The migration of epithelial cells in the modified Boyden chamber is measured using a conventional method. A polycarbonate filter membrane of μm aperture is coated at 4° C. for 24 h using collagen IV (10 μg/mL) and Matrigel (11 μg/filter). The Tca-8113, A549, Ncl-H446, and HepG2 cell lines are washed with DMEM culture solution to $2 \times 10^6$/mL. 200 μL of DMEM containing 5% FBS is added to the low part of the Boyden chamber as a chemoattractant, and followed by covering a polycarbonate filter membrane. 800 μL of a cell suspension is added to the upper part of the Boyden chamber, cultured at 37° C. at 5% $CO_2$ for 5 h. The device is disassembled and the membrane is collected. The cells are cleaned off, and the membrane is fixed with carbinol and stained with hematoxylin. Five fields of vision per membrane are observed under a 200× microscope. Subsequently, the number of migrating cells is calculated. Experiments show that the transfection of rAAV-antiCYP2J2 and the application of the CYP epoxygenase inhibitor 17-ODYA, can decrease the ability of migrating of cells, which is about 60% of basal state ($P<0.01$), as shown in FIGS. 14 A and B.

The result shows rAAV-anti2J2 virus and the CYP epoxygenase inhibitor (17-ODYA) have the ability to inhibit the proliferation and migration of tumor and can be used for tumor treatment. The recombinant adeno-associated virus expressing antisense human CYP2J2 gene (rAAV-anti2J2), which can be expressed for a long term in organisms, blocks the transcription and translation of CYP2J2 gene in gene level and decreases the expression of CYP2J2. The effect is more powerful. The clinical application of the recombinant adeno-associated virus expressing antisense human CYP2J2 gene (rAAV-anti2J2) and the epoxygenase inhibitor will play an important role for the treatment of diseases, for example, tumors.

Example 5

Influence of rAAV-anti2J2 Epoxygenase on the Apoptosis of Tumor Cells

Following the above-mentioned methods, four different kinds of tumor cell lines are transfected with rAAV-GFP, rAAV-anti2J2, rAAV-F87V, and rAAV-CYP2J2 respectively. A week later, TNFα is used to induce the apoptosis of tumor cells. The apoptosis is measured using different methods. Using DNA ladder, acridine orange staining, and flow cytometry analysis, it is found that: Both adding EETs directly and transfecting rAAV-CYP2J2 or rAAV-CYPF87V can decrease significantly the formation of DNA ladder, but either using epoxygenase inhibitor 17-ODYA or transfecting rAAV-anti2J2 promotes significantly the apoptosis of tumor cells induced by TNF-α. Stained with acridine orange or ethidium bromide, cells are observed that, under a fluorescent microscope, the group either transfected with epoxygenase gene or interfered directly with EETs has a small quantity of cells exfoliated, and the cell density is high, the number of apoptotic cells is significantly less than that in the control group. On the contrary, tumor cells transfected with 17-ODYA or rAAV-anti2J2 have obvious exfoliation, the density thereof decreases significantly, and most nuclear chromatins concentrated or broken into particles, the number of apoptotic cells is large. Thus, the EETs and epoxygenase gene resist the apoptosis of cancer cells induced by TNF-α. After PI staining and Annexin V-FITC/PI dobule staining separatively, the total apoptosis rate and early apoptosis rate of cells are calculated using flow cytometry.

The result shows that, the total apoptotic rate of the cells pretreated with three kinds of EETs is 14.94%±3.5, 11.72%±4.2 and 12.89%±2.7, respectively, which are significantly lower than that in the control group (28.15%±4.7, $P<0.01$) and the vehicle group (27.86%±6.1, $P<0.01$) and significantly lower than that in the 17-ODYA group (52.65%±3.6). The total apoptotic rate of tumor cells transfected with CYP2J2 and CYPF87V is 7.24%±4.2 and 7.79%±2.7, respectively, which is significantly lower than that in the control group (20.15%±3.5, $P<0.01$), the 17-ODYA group (33.51%±6.1, $P<0.01$), and the transfected rAAV-anti2J2 group (40.74%±3.5, $P<0.01$).

The research on the antiapoptosis mechanism of epoxygenase and EETs shows that EETs and transfecting epoxygenase gene can both promote the phosphorylation of Akt, increase the expression of antiapoptosis protein Bcl-2 and Bcl-xL, and decrease the expression of apoptosis protein Bax. However, using the CYP epoxygenase inhibitor or transfecting rAVV-anti2J2 has a completely opposite effect. The results show both epoxygenase and EETs can not only promote the growth of tumor, but also protect the tumor cells through inhibiting the cell apoptosis induced by TNF-α. According to the conclusion, using the CYP epoxygenase inhibitor or transfecting rAVV-anti2J2 can promote the apoptosis of tumor, thereby treating tumors.

What is claimed is:

1. A recombinant adeno-associated virus expressing antisense human CYP2J2 gene, the virus being deposited with the CCTCC and assigned accession number V200411.

* * * * *

SEQUENCE LISTING

```
<160> NUMBER OF SEQ ID NOS: 5

<210> SEQ ID NO 1
<211> LENGTH: 1800
<212> TYPE: DNA
<213> ORGANISM: Homo sapiens

<400> SEQUENCE: 1
ccacgcgtcc gcgccgcctg cttggaccgc agaagagcag gaggacgtct gagccatgct      60
cgcggcgatg ggctctctgg cggctgccct ctgggcagtg gtccatcctc ggactctcct     120
actgggcact gtcgccttc tgctcgctgc tgactttctc aaaagacggc gcccaaagaa     180
ctacccgccg gggccctggc gcctgccctt ccttggcaac ttcttccttg tggacttcga     240
gcagtcgcac ctggaggttc agctgtttgt gaagaaatat gggaaccttt ttagcttgga     300
gcttggtgac atatctgcag ttcttattac tggcttgccc ttaatcaaag aagcccttat     360
ccacatggac caaaactttg gaaccgccc cgtgacccct atgcgagaac atatctttaa     420
gaaaaatgga ttgattatgt caagtggcca ggcatggaag gagcaaagaa ggttcactct     480
gacagcacta aggaactttg gtttaggaaa gaagagctta gaggaacgca ttcaggagga     540
ggcccaacac ctcactgaag caataaaaga ggagaacgga cagccttttg accctcattt     600
caagatcaac aatgcagttt ccaatatcat ttgctccatc accttcggag aacgctttga     660
gtaccaggat agttggttc agcagctgct gaagttacta gatgaagtca catacttgga     720
ggcttcaaag acatgccagc tctacaatgt ctttccatgg ataatgaaat tcctgcctgg     780
accccaccaa actctcttca gcaactggaa aaaactgaaa ttgtttgttt ctcatatgat     840
tgacaaacac agaaaggatt ggaatcctgc agaaacaaga gactttattg atgcttacct     900
taaagaaatg tcaaagcaca caggcaatcc tacttcaagt ttccatgaag aaaacctcat     960
ctgcagcacc ctggacctct tctttgccgg aaccgagaca cttccacaa ctctgcgatg    1020 ggctctgctt tatatggccc tctacccaga aatccaagaa aaagtacaag ctgagattga    1080
cagagtgatt ggccaggggc agcagccgag cacagccgcc cgggagtcca tgccctacac    1140
```

-continued

```
caatgctgtc atccatgagg tgcagagaat gggcaacatc atcccctga acgttcccag    1200 ggaagtgaca gttgatacca ctttggctgg gtaccacctg cccaagggta ccatgatcct    1260
gaccaatttg acggcgctgc acagggaccc cacagagtgg gccacccctg acacattcaa    1320
tccggaccat tttctggaga atggacagtt taagaaaagg gaagccttta tgcctttctc    1380
aataggaaag cgggcatgcc tcggagaaca gttggccagg actgagctgt ttattttctt    1440
cacttccctt atgcaaaaat ttaccttcag gcccccaaac aatgagaagc tgagcctgaa    1500
gtttagaatg ggtatcacca tttcccccagt cagtcaccgc ctctgcgctg ttcctcaggt    1560
gtaatattgt taagaaagaa aggggcaagg aaagtaagaa acatggcac gtgttctgaa    1620 accactggtg tctgctcaga tgtgttggga caaaatgaaa gtgactttca agaaagatca    1680
gaggaatttg actcagagaa aactagatcc aaatcccagc tctactgtct cgtccgaatt    1740
agccttggga aaatcattta tatgctaaat aatttacctt tttatctagg agatgaaaag    1800
```

<210> SEQ ID NO 2
<211> LENGTH: 4675
<212> TYPE: DNA
<213> ORGANISM: adeno-associated virus 2

<400> SEQUENCE: 2

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacgg gcatctgccc ggcatttctg acagctttgt gaactgggtg gccgagaagg     420
aatgggagtt gccgccagat tctgacatgg atctgaatct gattgagcag gcacccctga     480
ccgtggccga aagctgcag cgcgactttc tgacggaatg gcgccgtgtg agtaaggccc     540
cggaggccct tttctttgtg caatttgaga agggagagag ctacttccac atgcacgtgc     600
tcgtggaaac caccggggtg aaatccatgg ttttgggacg tttcctgagt cagattcgcg     660
aaaaactgat tcagagaatt taccgcggga tcgagccgac tttgccaaac tggttcgcgg     720
tcacaaagac cagaaatggc gccggaggcg ggaacaaggt ggtggatgag tgctacatcc     780
ccaattactt gctccccaaa acccagcctg agctccagtg ggcgtggact aatatggaac     840
agtatttaag cgcctgtttg aatctcacgg agcgtaaacg gttggtggcg cagcatctga     900
cgcacgtgtc gcagacgcag gagcagaaca aagagaatca gaatcccaat ctgatgcgc     960 cggtgatcag atcaaaaact tcagccaggt acatggagct ggtcgggtgg ctcgtggaca    1020 agggattac ctcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa attttggaac taaacgggta cgatcccca tatgcggctt    1260 ccgtctttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact ttccctttca cgactgtgtc gacaagatgg    1440
tgatctggtg ggaggagggg aagatgaccg ccaaggtcgt ggagtcggcc aaagccattc    1500
```

```
tcggaggaag caaggtgcgc gtggaccaga aatgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agacttttc cggtgggcaa    1740 aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaaggcgta tcagaaactg tgctacattc    2100
atcatatcat gggaaaggtg ccagacgctt gcactgcctg cgatctggtc aatgtggatt    2160
tggatgactg catctttgaa caataaatga tttaaatcag gtatgctgcc gatggttat    2220 cttccagatt ggctcgagga cactctctct gaggaataaa gacagtggtg gaagctcaaa    2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgta caaagcctac gaccggcagc tcgacagcgg    2460
agacaacccg tacctcaagt acaaccacgc cgacgcggag tttcaggagc gccttaaaga    2520
agatacgtct tttgggggca acctcggacg agcagtcttc caggcgaaaa agagggttct    2580
tgaacctctg ggcctggttg aggaacctgt taagacggct ccgggaaaaa agaggccggt    2640
agagcactct cctgtggagc cagactcctc ctcgggaacc ggaaaggcgg ccagcagcc    2700 tgcaagaaaa agattgaatt ttggtcagac tggagacgca gactcagtac ctgaccccca    2760
gcctctcgga cagccaccag cagcccccte tggtctggga actaatacga tggctacagg    2820
cagtggcgca ccaatggcag acaataacga gggcgccgac ggagtgggta attcctccgg    2880
aaattggcat tgcgattcca catggatggg cgacagagtc atcaccacca gcacccgaac    2940
ctgggccctg cccacctaca caaccaccct ctacaaacaa atttccagcc aatcaggagc    3000
ctcgaacgac aatcactact ttggctacag cacccccttgg gggtattttg acttcaacag    3060
attccactgc cacttttcac cacgtgactg gcaaagactc atcaacaaca actggggatt    3120
ccgacccaag agactcaact tcaagctctt taacattcaa gtcaaagagg tcacgcagaa    3180
tgacggtacg acgacgattg ccaataacct taccagcacg gttcaggtgt ttactgactc    3240
ggagtaccag ctcccgtacg tcctcggctc ggcgcatcaa ggatgcctcc cgccgttccc    3300
agcagacgtc ttcatggtgc cacagtatgg ataccttcacc ctgaacaacg ggagtcaggc    3360
agtaggacgc tcttcatttt actgcctgga gtactttcct tctcagatgc tgcgtaccgg    3420
aaacaacttt accttcagct cacttttga ggacgttcct ttccacagca gctacgctca    3480
cagccagagt ctggaccgtc tcatgaatcc tctcatcgac cagtacctgt attacttgag    3540
cagaacaaac actccaagtg gaaccaccac gcagtcaagg cttcagtttt ctcaggccgg    3600
agcgagtgac attcgggacc agtctaggaa ctggcttcct ggaccctgtt accgccagca    3660
gcgagtatca aagacatctg cggataacaa caacagtgaa tactcgtgga ctggagctac    3720
caagtaccac ctcaatggca gagactctct ggtgaatccg gccatggcaa gccacaagga    3780
cgatgaagaa aagttttttc ctcagagcgg ggttctcatc tttgggaagc aaggctcaga    3840
gaaaacaaat gtgaacattg aaaaggtcat gattacagac gaagaggaaa tcggaacaac    3900
```

```
caatcccgtg gctacggagc agtatggttc tgtatctacc aacctccaga gaggcaacag    3960
acaagcagct accgcagatg tcaacacaca aggcgttctt ccaggcatgg tctggcagga    4020
cagagatgtg taccttcagg ggcccatctg ggcaaagatt ccacacacgg acggacattt    4080
tcacccctct cccctcatgg gtggattcgg acttaaacac cctcctccac agattctcat    4140
caagaacacc ccggtacctg cgaatccttc gaccaccttc agtgcggcaa agtttgcttc    4200
cttcatcaca cagtactcca cgggacacgg tcagcgtgga gatcgagtgg gagctgcaga    4260
aggaaaacag caaacgctgg aatcccgaaa ttcagtacac ttccaactac aacaagtctg    4320
ttaatcgtgg acttaccgtg gatactaatg gcgtgtattc agagcctcgc cccattggca    4380
ccagatacct gactcgtaat ctgtaattgc ttgttaatca ataaaccgtt taattcgttt    4440
cagttgaact ttggtctctg cgtatttctt tcttatctag tttccatggc tacgtagata    4500
agtagcatgg cgggttaatc attaactaca aggaacccct agtgatggag ttggccactc    4560
cctctctgcg cgctcgctcg ctcactgagg ccgggcgacc aaaggtcgcc cgacgcccgg    4620
gctttgcccg ggcggcctca gtgagcgagc gagcgcgcag agagggagtg gccaa         4675
```

```
<210> SEQ ID NO 3
<211> LENGTH: 145
<212> TYPE: DNA
<213> ORGANISM: adeno-associated virus 2

<400> SEQUENCE: 3
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag agagggagtg gccaa                                          145

<210> SEQ ID NO 4
<211> LENGTH: 26
<212> TYPE: DNA
<213> ORGANISM: Artificial Sequence
<220> FEATURE:
<223> OTHER INFORMATION: Fully synthetic PCR upsteam primer amplifying
      CYP2J2 cDNA, synthesized by Wuhan Biosynthesis Co.

<400> SEQUENCE: 4
gcccggaatt caaaatgatt ctcaac                                          26

<210> SEQ ID NO 5
<211> LENGTH: 30
<212> TYPE: DNA
<213> ORGANISM: Artificial Sequence
<220> FEATURE:
<223> OTHER INFORMATION: Fully synthetic PCR downsream primer amplifying
      CYP2J2 cDNA, synthesized by Wuhan Biosynthesis Co.

<400> SEQUENCE: 5
ggcgcacaag ctttcaaata agagtataac                                      30
```